United States Patent
Patoiseau et al.

(10) Patent No.: US 6,303,603 B1
(45) Date of Patent: Oct. 16, 2001

(54) 3-OXO-2(H)-1,2,4-TRIAZINE DERIVATIVES AS LIGANDS OF 5 $HT_{1A}$ RECEPTORS

(75) Inventors: Jean-Francois Patoiseau; Elisabeth Dupont-Passelaigue, both of Castres; Wouter Koek, Viviers-les Montagnes, all of (FR)

(73) Assignee: Pierre Fabre Medicament, Boulogne (FR)

(*) Notice: Subject to any disclaimer, the term of this patent is extended or adjusted under 35 U.S.C. 154(b) by 0 days.

(21) Appl. No.: 09/529,728

(22) PCT Filed: Oct. 14, 1998

(86) PCT No.: PCT/FR98/02205

§ 371 Date: Apr. 14, 2000

§ 102(e) Date: Apr. 14, 2000

(87) PCT Pub. No.: WO99/20622

PCT Pub. Date: Apr. 29, 1999

(30) Foreign Application Priority Data

Oct. 16, 1997 (FR) .................................................. 97 12955

(51) Int. Cl.[7] ........................... A61K 31/53; A61P 25/18; C07D 253/06
(52) U.S. Cl. ........................................... 514/242; 544/182
(58) Field of Search ............................... 544/182; 514/242

(56) References Cited

FOREIGN PATENT DOCUMENTS

| WO9501965 | 1/1995 | (WO) . |
|---|---|---|
| WO9616949 | 6/1996 | (WO) . |

Primary Examiner—Richard L. Raymond
Assistant Examiner—Venkataraman Balasubramanian
(74) Attorney, Agent, or Firm—The Firm of Hueschen and Sage; G. Patrick Sage

(57) ABSTRACT

The invention concerns novel 3-oxo-(2H)-1,2,4-triazine derivatives of general formula (I) in which $R_1$ represents: hydrogen, when A is an optionally substituted nitrogen atom; a linear or branched $_1$–$C_4$ alkyl group; a $C_1$–$C_4$ phenyl alkyl group, the phenyl ring being optionally substituted by one or several groups such as $C_1$–$C_4$ alkyl, $C_1$–$C_3$ alkoxy, halogen, trifluoromethyl. $R_2$ represents: hydrogen; a linear or branched $C_1$–$C_4$ alkyl radical; a $C_{1-C4}$ phenyl or phenylalkyl group, the phenyl ring being optionally substituted by one or several groups such as $C_1$–$C_4$ alkyl, $C_1$–$C_3$ alkoxy, halogen, trifluoromethyl. A represents an oxygen atom or a nitrogen atom optionally $NR_3$ substituted. $R_3$ represents hydrogen or a methyl group. B represents a group such as (IIa) in which Ar itself represents an aromatic structure such as phenyl, pyridyl or pyrimidyl, optionally substituted by one or several groups such as $C_1$–$C_3$ alkyl, $C_1$–$C_3$ alkoxy, hydroxy, trifluoromethyl or halogen and n can be whole numbers ranging between 3 and 5; (IIb) in which Ar is as defined in formula (IIa) and m can be a whole number ranging between 1 and 2; (IIc) in which $R_4$ represents hydrogen or a $C_1$–$C_3$ alkyl group and n can be whole numbers ranging between 3 and 5.

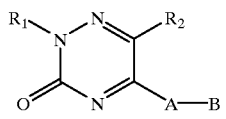

(I)

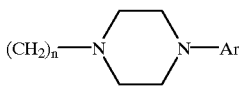

(IIa)

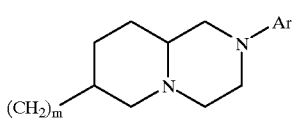

(IIb)

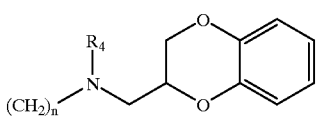

(IIc)

7 Claims, No Drawings

3-OXO-2(H)-1,2,4-TRIAZINE DERIVATIVES AS LIGANDS OF 5 HT$_{1A}$ RECEPTORS

This is a 371 filing of PCT/FR98/02205 filed Oct. 14, 1998.

A subject-matter of the present invention is novel 3-oxo-(2H)-1,2,4-triazine derivatives functionalized in the 5 position, their preparation and their application in therapeutics.

5-HT$_{1A}$ receptors have been claimed for their role in various pathologies, such as hypertension, sexual dysfunctioning, anorexia or memory. The main target suggesting the involvement of the 5-HT$_{1A}$ receptors is, however, composed of disorders of the central nervous system, such as anxiety and depression. The hypotheses, supported by tests on animal models and clinical studies, suggest that more effective treatments of these pathologies can be envisaged with 5-HT$_{1A}$ agonist compounds with a high affinity which are very selective and highly effective.

3,5-Dioxo-(2H,4H)-1,2,4-triazine derivatives and 3,5-dioxo-6-amino-(2H,4H)-1,2,4-triazine derivatives have been claimed previously by the Applicant Company (FR 2,707,294 of Jun. 7, 1993 and FR 2,727,682 of Feb. 12, 1994).

The compounds of the present invention are characterized by their powerful affinity with regard to the 5-HT$_{1A}$ receptor in combination with a high selectivity, in particular with regard to D$_2$ and α$_1$ receptors, and a high intrinsic activity.

The compounds of the invention correspond to the general formula I

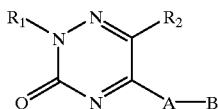

I in which

R$_1$ represents:
   hydrogen, when A is an optionally substituted nitrogen atom
   a linear or branched C$_1$–C$_4$ alkyl group
   a C$_1$–C$_4$ phenylalkyl group, the phenyl nucleus optionally being substituted by one or more groups, such as C$_1$–C$_4$ alkyl, C$_1$–C$_3$ alkoxy, halogen or trifluoromethyl, R$_2$ represents:
   hydrogen
   a linear or branched C$_1$–C$_4$ alkyl radical
   a C$_1$–C$_4$ phenyl or phenylalkyl group, the phenyl nucleus optionally being substituted by one or more groups, such as C$_1$–C$_4$ alkyl, C$_1$–C$_3$ alkoxy, halogen or trifluoromethyl, A represents an oxygen atom or an optionally substituted nitrogen atom NR$_3$, R$_3$ represents hydrogen or a methyl group, B represents a group of type

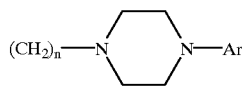

IIa in which Ar itself represents an aromatic structure, such as phenyl, pyridyl or pyrimidyl, optionally substituted by one or more groups, such as C$_1$–C$_3$ alkyl, C$_1$–C$_3$ alkoxy, hydroxyl, trifluoromethyl or halogen, and n can take the integral values from 3 to 5,

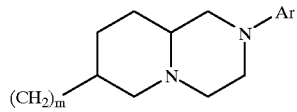

IIb in which Ar is as defined in the formula IIa and m can take the integral values 1 and 2,

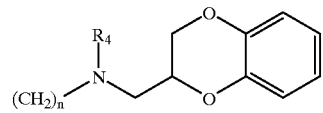

IIc in which R4 represents hydrogen or a C$_1$–C$_3$ alkyl group and n can take the integral values from 3 to 5.

The invention covers the inorganic or organic salts of compounds of general formula I with pharmaceutically acceptable acids.

In addition, it covers the various enantiomers and diastereoisomers of the compounds which have one or more asymmetric carbons, as well as their mixtures in all proportions, including in particular the racemic mixtures.

Synthesis

The compounds of the present invention can be prepared according to various methods. They can be synthesized by using the synthetic routes described hereinbelow or by using synthetic methods known to a person skilled in the art.

The synthesis of the compounds of general formula I is characterized in that a derivative of general formula III (Scheme 1)

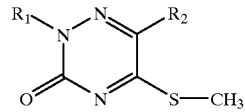

III is condensed with an alcohol B-OH IV or an amine BHNR$_3$ V, R$_1$, R$_2$, R$_3$ and B having the same meaning as above in the general formula I.

The compounds III are obtained according to a process (Scheme 1) characterized by the following stages:

1—Condensation of glyoxylic acid with thiosemicarbazide, followed by a basic treatment, such as sodium hydroxide solution, 2—Methylation by methyl iodide in basic aqueous medium, followed by an acidic treatment, such as hydrochloric acid, 3—Sulfuration of the 5 position in the presence of Lawesson's reagent in a solvent such as pyridine, 4—Methylation by methyl iodide in basic aqueous medium, such as sodium hydroxide solution, 5—Alkylation of the 2 position by an alkyl halide $R_1X$ in the presence of NaH in DMF, X representing Cl, Br or Synthesis of the Compounds III (Scheme 1)

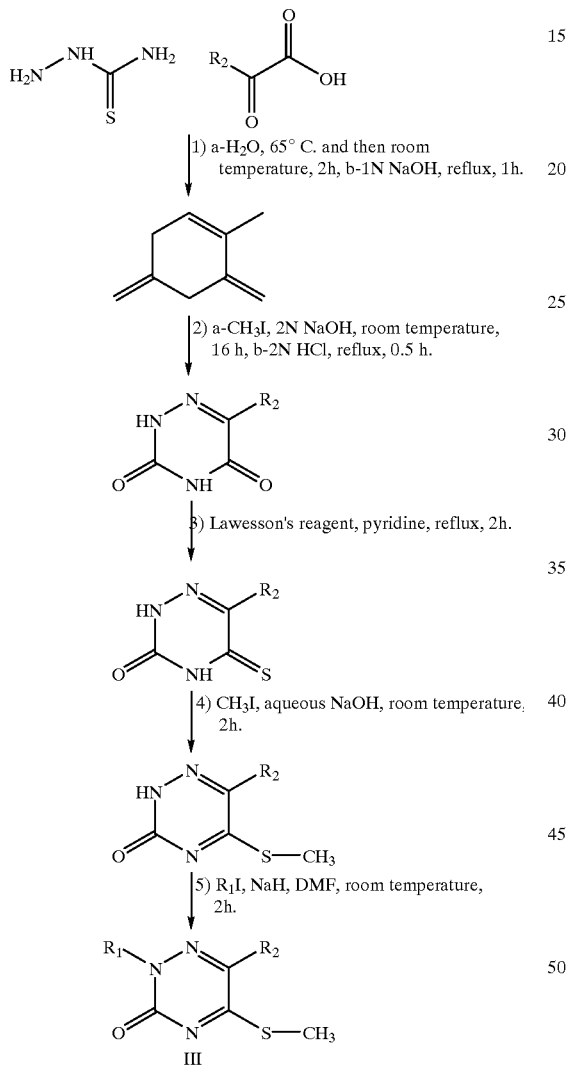

The condensation of intermediates III with the alcohols IV or amines V is carried out in the presence of a base, such as sodium hydride or potassium tert-butoxide in dioxane, THF or toluene.

The optional separation of the enantiomers or diastereoisomers of compounds having one or more asymmetric carbons is generally carried out on the final products by liquid chromatography on a chiral column.

Synthesis of the Alcohols B-OH IV

A—When B represents a group of type

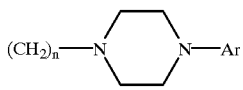

IIa the corresponding alcohols

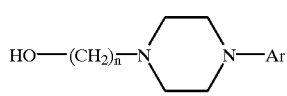

IVa can be obtained 1) by treating the piperazine

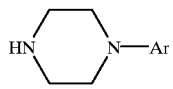

VI with a haloalcohol $$HO-(CH_2)_n-Hal \qquad \text{VII}$$

in the presence of $K_2CO_3$ and optionally of KI, when Hal=Br or Cl, in acetonitrile at reflux, 2) when n=4 or 5, by treating the piperazine VI with a lactone VIII

VIII in the presence of a Lewis acid, such as $AlCl_3$, and of triethylamine in dichloromethane, and by then reducing the amide IX formed

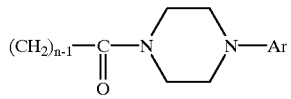

IX with a hydride, such as $LiAlH_4$ in THF, 3) when Ar represents a heterocycle of pyrimidine type, by treating optionally substituted 2-chloropyrimidine with a hydroxyalkylpiperazine X

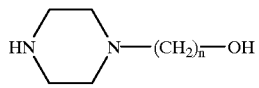

X bin a solvent, such as toluene, in the presence of an amine, such as triethylamine.

B—When B represents a group of type

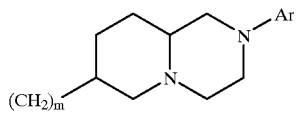
IIb 1) when m=1, according to the process disclosed in the Pfizer Patent WO 93 25552 (1992), 2) when m=2, by oxidizing the alcohol XI

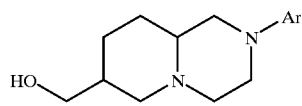
XI under the Swern conditions and by then treating the aldehyde obtained XII

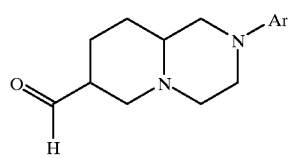
XII with a Wittig reagent, such as methoxymethyltriphenylphosphonium chloride in TrHF, followed by the hydrolysis in aqueous acidic medium of the enol ether obtained XIII

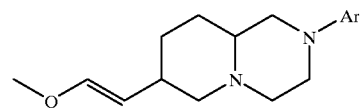
XIII to result in the corresponding aldehyde XIV

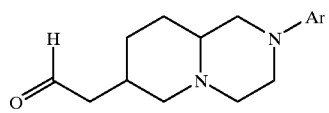
XIV which is reduced to the alcohol with a hydride, such as $NaBH_4$ in ethanol.

C—When B represents a group of type

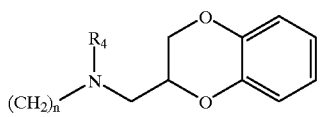
IIc the corresponding alcohols

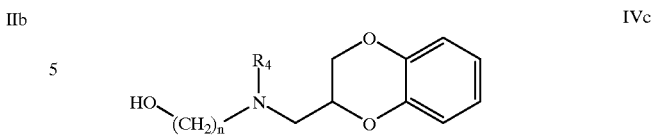
IVc can be prepared 1) by treating benzodioxanemethylamine according to the process described in paragraph A-2, 2) by condensing benzodioxanemethanol with an aminoalcohol XV

$HO-(CH_2)_n-NH_2$    XV

Synthesis of the Amines $B-NHR_3$ V

1) When $R_3=H$, the compounds V are commercial amines or can be obtained conventionally, such as generation of the primary amine from the intermediate phthalimide.

2) When $R_3=Me$, the compounds are obtained from the amines $BNH_2$ (the method of preparation of which is described hereinabove) by formylating the amine with formic anhydride in a solvent, such as pyridine, to result in the formamide XVI

XVI which is reduced with a hydride, such as $LiAlH_4$ in THF.

The following examples illustrate the invention without limiting the scope thereof.

The elemental analyzes and the IR and NMR spectra confirm the structures of the compounds obtained according to the invention.

EXAMPLE 1

2-Methyl-5-[4-(4-pyrimidin-2-yl-piperazin-1-yl) Butoxyl-2H-[1,2,4]Triazin-3-One (1)

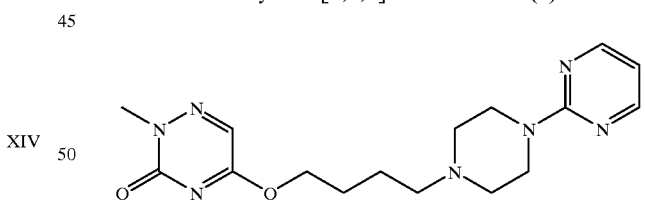

a) 5-Thioxo-4,5-dihydro-2H-[1,2,4]triazin-3-one (1a)

98.3 g (243 mnol) of Lawesson's reagent are added to a solution of 2H-[1,2,4]triazin-3,5-dione (50 g, 442 mmol) in 400 ml of pyridine. The mixture is brought to reflux for 4 h. After evaporating the solvent under reduced pressure, the residue obtained is taken up in 400 ml of water. The brown precipitate which forms is isolated by filtration. These crystals are taken up in $H_2O$ and extracted with ethyl acetate. After drying the organic phases ($MgSO_4$) and concentrating them to dryness, yellow crystals are obtained.

Retreatment of the aqueous solution (400 ml) by extracting with ethyl acetate makes it possible to isolate a further solid fraction. In total, after drying, 60 g of yellow crystals are obtained.

M.p.=239° C.; TLC, 60 F 254 Merck silica gel; $CH_2Cl_2$/MeOH: 90/10, Rf=0.4.

b) 5-Methylsulfanyl-2H-[1,2,4]triazin-3-one (1b)

The compound 1a (30 g, 232 mmol) and $CH_3I$ (15.9 ml, 255 mmol) are placed in 300 ml of water. 18.6 g of NaOH (465 mmol) are added and the mixture is stirred for 1 h at room temperature. The reaction mixture, cooled on a bed of ice, is neutralized using 27 ml of acetic acid and then extracted with dichloromethane. The organic phases are dried ($MgSO_4$) and then concentrated to dryness. After recrystallizing from ether, 29.9 g of compound 1b are isolated.

M.p.=171° C.; TLC, 60 F 254 Merck silica gel; $CH_2Cl_2$/MeOH: 90/10, Rf=0.5.

c) 2-Methyl-5-methylsulfanyl-2H-[1,2,4]triazin-3-one (1c)

A suspension, placed under nitrogen, of NaH (60% in liquid paraffin, 4.4 g, 110 mmol) in 50 ml of DMF is cooled to 0° C. on a bed of ice. The compound 1b (15.9 g, 111 mmol), diluted in 100 ml of DMF, is run into this suspension dropwise. The mixture is subsequently stirred for 1 h at room temperature.

After concentrating the reaction mixture to dryness, the residue is taken up in $H_2O$ and extracted with $CH_2Cl_2$. The organic phases are dried over $MgSO_4$ and then evaporated under reduced pressure.

After crystallizing from EtOH/isopropyl ether and then drying, 13.9 g of product 1c are isolated in the form of beige crystals.

M.p.=106° C.; TLC, 60 F 254 Merck silica gel; $CH_2Cl_2$/MeOH: 95/5, Rf=0.52.

d) 4-Hydroxy-1-(4-pyrimidin-2-yl-piperazin-1-yl)butan-1-one (1d)

$AlC_3$ (18.5 g, 138.8 mmol) is suspended in 100 ml of dichloromethane under an inert atmosphere ($N_2$). A solution of triethylamine (22.3 ml, 160 mmol) diluted in 40 ml of dichloroethane is run dropwise onto this mixture cooled to 0° C. on a bed of ice.

This mixture is brought back to room temperature and then a solution of 2-pyrimidinylpiperazine (19.5 g, 119 mmol) and butyrolactone (8.2 ml, 107 mmol) in 80 ml of dichloroethane is added dropwise.

This mixture is stirred for 2 h at room temperature and then poured quickly onto 200 ml of ice. After extracting with dichloromethane, drying the organic phases ($MgSO_4$) and concentrating them to dryness, 27 g of crystals are recovered and are used in the following stage without additional purification.

e) 4-4-Pyrimidin-2-yl-piperazin-1-yl)butan-1-ol (1e)

$LiAlH_4$ (4.9 g, 129 mmol) is suspended in 100 ml of THF under nitrogen. 1d (27 g, 108 mmol), diluted in 150 ml of THF, is added dropwise while taking care to maintain the temperature at room temperature. This mixture is stirred for 1 h, hydrolyzed with the minimum amount of water and dried over $MgSO_4$. After filtering off the aluminum salts, the filtrate is concentrated to dryness. The residue obtained is purified by silica flash chromatography (eluent: $CH_2Cl_2$/MeOH: 95/5).

17.3 g of yellow oil are recovered. After salifying with fumaric acid in ethanol, a white solid is isolated.

M.p.=112° C.; TLC, 60 F 254 Merck silica gel; $CH_2Cl_2$/MeOH/$NH_4OH$: 90/9/1, Rf=0.54.

f) 2-Methyl-5-[4-(4-pyrimidin-2-yl-piperazin-1-yl)butoxy]-2H-[1,2,4]triazin-3-one (1)

NaH (60% in liquid paraffin, 0.68 g, 17 mmol) is placed in dimethoxyethane (DME) under an inert atmosphere. A solution of compound 1e (in the base form, 4.5 g, 19 mmol) diluted in 20 ml of DME is added dropwise to this mixture cooled to 0° C.

The reaction mixture is stirred for 1 h at room temperature and then brought back to 0° C. A solution of 1c (3 g, 19.1 mmol) diluted in 40 ml of DME is then run n dropwise. The temperature of the reaction mixture is subsequently brought back to room temperature and stirring is maintained for 1 h.

The inorganic products are filtered off under vacuum and the filtrate is concentrated to dryness. The residue obtained is purified by silica flash chromatography (eluent: $CH_2Cl_2$/MeOH: 95/5), which makes it possible to isolate a yellow oil which crystallizes.

After recrystallizing from acetone, 2 g of compound 1 are obtained.

M.p.=134° C.; TLC, 60 F 254 Merck silica gel; $CH_2Cl_2$/MeOH: 90/10, Rf=0.46.

EXAMPLE 2

2-Methyl-5-[4-[4-(4-methylpyrimidin-2-yl)piperazin-1-yl]butoxyl]-2H-[1,2,4]triazin-3-one fumarate (2)

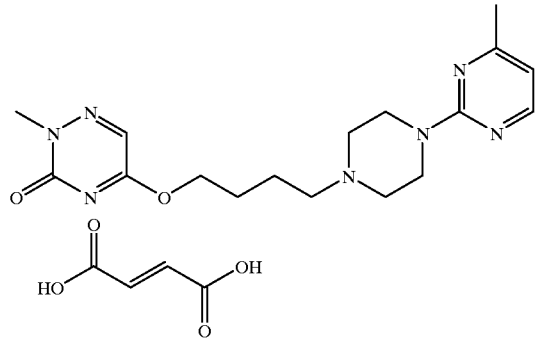

a) 4-[4-(4-Methylpyrimidin-2-yl)piperazin-1-yl]butan-1-ol (2a)

4-Methyl-2-piperazin-1-yl-pyrimidine dihydrochloride (7 g, 38.8 mmol) and 4-chlorobutanol (4.6 ml, 46 mmol) are placed in 150 ml of acetonitrile in the presence of $K_2CO_3$ (21.5 g, 155.5 mmol). This mixture is brought to reflux for 16 h. After cooling, the inorganic products are removed by filtration and the filtrate is concentrated to dryness.

The residue obtained is purified by silica flash chromatography (eluent: $CH_2Cl_2$/MeOH: 90/10). 4.7 g of white crystals are obtained.

M.p.=76° C.; TLC, 60 F 254 Merck silica gel; $CH_2Cl_2$/MeOH: 90/10, Rf=0.41.

b) 2-Methyl-5-[4-[4-(4-methylpyrimidin-2-yl)piperazin-1-yl]butoxy]-2H-[1,2,4]triazin-3-one fumarate (2)

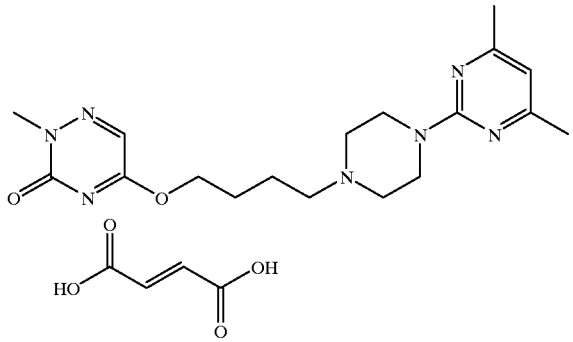

This compound is prepared according to the process described in Stage f of Example 1 using 4-[4-(4- methylpyrimidin-2-yl)piperazin-1-yl]butan-1-ol and then salified with fumaric acid in ethanol.

M.p.=144° C.; TLC, 60 F 254 Merck silica gel; CH$_2$Cl$_2$/MeOH/NH$_4$OH: 90/9/1, Rf=0.7.

EXAMPLE 3

5-[4-[4-(4,6-Dimethylpyrimidin-2-yl)piperazin-1-yl]butoxy]-2-methyl-2H-[1,2,4]triazin-3-one fumarate (3)

This compound is prepared according to the process described in Stage f of Example 1 using 4-[4-(4,6-dimethylpyrimidin-2-yl)piperazin-1-yl]butan-1-ol (prepared according to Process 2a) and THF, and then salified with fumaric acid in ethanol.

M.p.=180° C.; TLC, 60 F 254 Merck silica gel; CH$_2$Cl$_2$/MeOH/NH$_4$OH: 90/9/1, Rf=0.61.

EXAMPLE 4

5-[4-[4-(4-Methoxypyrimnidin-2-yl)piperazin-1-yl]butoxy]-2-methyl-2H-[1,2,4]triazin-3-one fumarate 4)

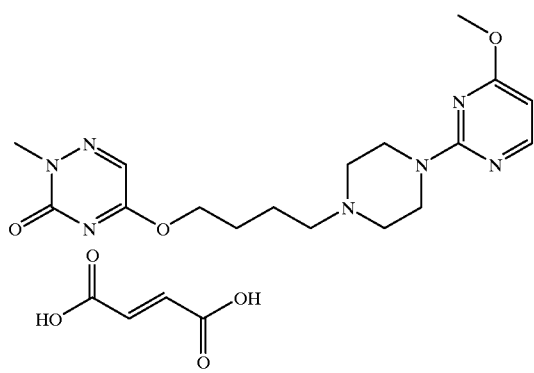

This compound is prepared according to the process described in Stage f of Example 1 using 4-[4-(4-methoxypyrimidin-2-yl)piperazin-1-yl]butan-1-ol (prepared according to Process 2a) and THF, and then salified with fumaric acid in ethanol.

M.p.=164° C.; TLC, 60 F 254 Merck silica gel; CH$_2$Cl$_2$/MeOH/NH$_4$OH: 90/9/1, Rf=0.6.

EXAMPLE 5

5-[4-[4-(5-Methoxypyrimidin-2-yl)piperazin-1-yl]butoxyl-2-methyl-2H-[1,2,4]triazin-3-one (5)

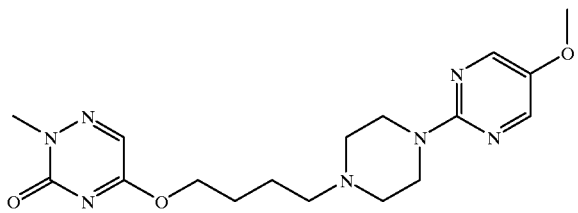

This compound is prepared according to the process described in Stage f of Example 1 using 4-[4-(5-methoxypyrimidin-2-yl)piperazin-1-yl]butan-1-ol (prepared according to Process 2a) and dioxane.

M.P.=101° C.; TLC, 60 F 254 Merck silica gel; CH$_2$Cl$_2$/MeOH: 90/10, Rf=0.58.

EXAMPLE 6

5-[4-[4-(4-Chloropyrimidin-2-yl)piperazin-1-yl]butoxy]-2-methyl-2H-[1,2,4]triazin-3-one (6)

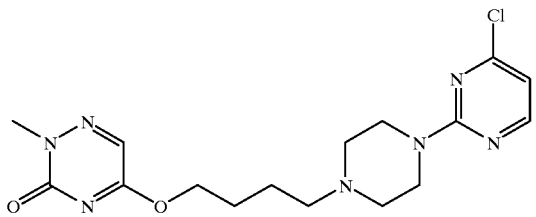

4-Piperazin-1-yl-butan-1-ol (6a)

Piperazine (50 g, 580 mmol) is placed in 500 ml of acetonitrile and the mixture is heated to 60° C. K$_2$CO$_3$ (96 g, 694 mmol) is added and the reaction mixture is brought to reflux. 4-Chlorobutanol (58 ml, 581 mmol) is then run in dropwise and then reflux is maintained for 4 h.

After filtering off the inorganic products, the filtrate is concentrated to dryness under vacuum. The residue obtained is purified by silica flash chromatrography (eluent: CH$_2$Cl$_2$/MeOH/NH$_{4OH}$: 80/18/2) and 51 g of a light-colored oil 6a are recovered.

TLC, 60 F 254 Merck silica gel; CH$_2$Cl$_2$/MeOH/NH$_4$OH: 80/18/2, Rf=0.40.

b) 4-[4-(4-Chloropyrimidin-2-yl)piperazin-1-yl]butan-1-ol (6b)

The compound 6a (30 g, 189 mmol) and triethylamine (31.6 ml, 226 mmol) are placed in toluene and then the mixture is brought to reflux. 2,4-Dichloropyrimidine (28.2 g, 189 mmol) is then added and reflux is maintained for 3 h.

After concentrating the reaction mixture to dryness, the residue is taken up in H$_2$O saturated with NaHCO$_3$ and is extracted with dichloromethane. The organic phases are dried over MgSO$_4$ and then concentrated to dryness. The residue obtained is purified by silica flash chromatography (eluent: CH$_2$Cl$_2$/MeOH: 95/5) and 9.13 g of product 6b are recovered in the form of an oil.

TLC, 60 F 254 Merck silica gel; CH$_2$Cl$_2$/MeOH: 95/5, Rf=0.56.

c) 5-(4-[4-(4-Chloropyrimidin-2-yl)piperazin-1-yllbutoxy]-2-methyl-2H-[1,2,4]triazin-3-one (6)

This compound is prepared according to the process described in Stage f of Example 1 using 4-[4-(4-chloropyrimidin-2-yl)piperazin-1-yl]butan-1-ol 6b and THF.

M.p.=96° C.; TLC, 60 P 254 Merck silica gel; CH$_2$Cl$_2$/MeOH/NH$_4$OH: 90/9/1, Rf=0.6.

EXAMPLE 7

5-[4-[4-(5-Fluoropyrimidin-2-yl)piperazin-1-yl]butoxy]-2-methyl-2H-[1,2,4]triazin-3-one (7)

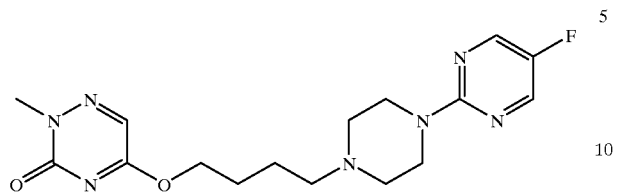

This compound is prepared according to the process described in Example 6 using, in Stage b, 5-fluoro-2-chloropyrimidine.

M.p.=102° C.; TLC, 60 F 254 Merck silica gel; $CH_2Cl_2$/MeOH: 90/10, Rf=0.46.

EXAMPLE 8

2-Propyl-5-(4-(4-pyrimidin-2-yl-piperazin-1yl)butoxy]-2H-([1,2,4]triazin-3-one fumarate (8)

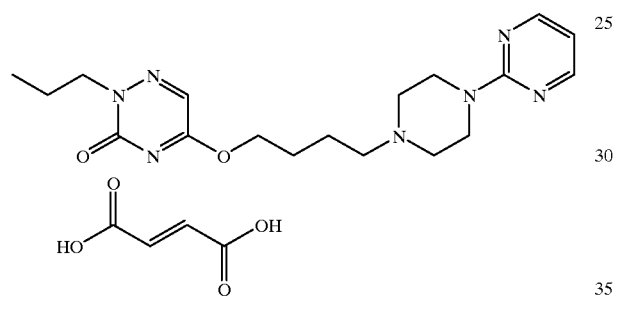

This compound is prepared according to the process described in Stage f of Example 1 using 4-(4-pyrimidin-2-yl-piperazin-1-yl)butan-1-ol (prepared according to Example 2a) and 2-propyl-5-methylsulfanyl-2H-[1,2,4]triazin-3-one (prepared according to Example 1c using propyl iodide) in THF, and then salified with fumaric acid in ethanol.

M.p.=131° C.; TLC, 60 F 254 Merck silica gel; $CH_2Cl_2$/MeOH/$NH_4OH$: 90/9/1, Rf=0.55.

EXAMPLE 9

2,6-Dimethyl-5-(4-(4-pyrimidin-2-yl-piperazin-1-yl)butoxy]-2H-[1,2,4]triazin-3-one (9)

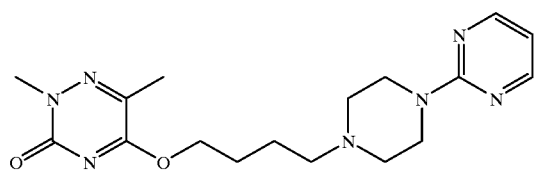

This compound is prepared according to the process described in Example 1 using 6-methyl-2H-[1,2,4]triazin-3,5-dione in Stage a and 4-(4-pyrimidin-2-yl-piperazin-1-yl)butan-1-ol (prepared according to Process 2a) and dioxane in Stage f.

M.p.=69° C.; TLC, 60 F 254 Merck silica gel; $CH_2Cl_2$/MeOH: 90/10, Rf=0.47.

EXAMPLE 10

2-Methyl-6-phenyl-5-[4-(4-pyrimidin-2-yl-piperazin-1-yl)butoxy]-2H-[1,2,4]triazin-3-one (10)

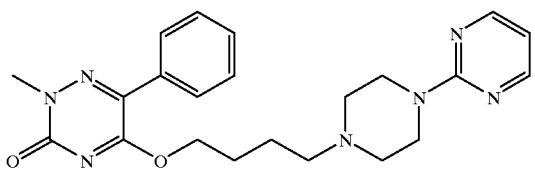

This compound is prepared according to the process described in Example 1 using 6-phenyl-2H-[1,2,4]triazin-3,5-dione in Stage a and 4-(4-pyrimidin-2-yl-piperazin-1-yl)butan-1-ol (prepared according to Process 2a) and dioxane in Stage f.

M.p.=99° C.; TLC, 60 F 254 Merck silica gel; $CH_2Cl_2$/MeOH: 90/10, Rf=0.48.

EXAMPLE 11

2-Methyl-6-benzyl-5-[4-(4-pyrimidin-2-yl-piperazin-1-yl)butoxyl]-2H-[1,2,4]triazin-3-one (11)

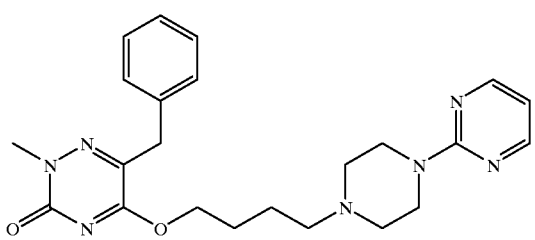

This compound is prepared according to the process described in Example 1 using 6-benzyl-2H-[1,2,4]triazin-3,5-dione in Stage a and 4-(4-pyrimidin-2-yl-piperazin-1-yl)butan-1-ol (prepared according to Process 2a) and dioxane in Stage f.

M.p.=86° C.; TLC, 60 F 254 Merck silica gel; $CH_2Cl_2$/MeOH: 90/10, Rf=0.33.

EXAMPLE 12

2-Benzyl-5-[4-(4-pyrimidin-2-yl-piperazin-1-yl)butoxy]-2H-[1,2,4]triazin-3-one (12)

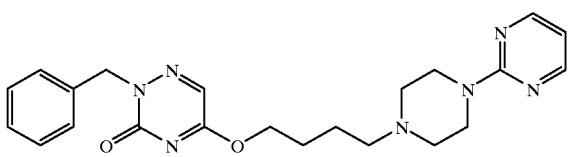

This compound is prepared according to the process described in Example 1 using benzyl chloride in Stage c and 4-(4-pyrimidin-2-yl-piperazin-1-yl)butan-1-ol (prepared according to Process 2a) and dioxane in Stage f.

M.p.=86° C.; TLC, 60 F 284 Merck silica gel; $CH_2Cl_2$/MeOH: 90/10, Rf=0.38.

EXAMPLE 13

2-Methyl-5-[3-(4-pyrimidin-2-yl-piperazin-1-yl) propoxy]-2H-[1,2,4]triazin-3-one fumarate (13)

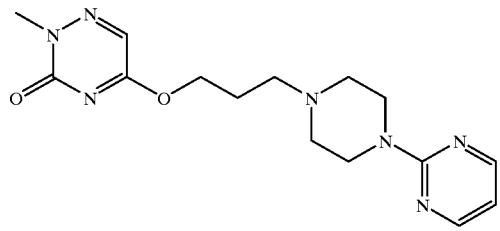

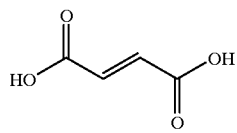

This compound is prepared according to the process described in Example 1, Stage f, using 4-(4-pyrimidin-2-yl-piperazin-1-yl)propan-1-ol (prepared according to Process 2a from 3-chloropropanol) and dioxane, and then salified with fumaric acid in methanol.

M.p.=167° C.; TLC, 60 F 254 Merck silica gel; $CH_2Cl_2$/MeOH/$NH_4OH$: 90/9/1, Rf=0.60.

EXAMPLE 14

2-Methyl-5-[5-(4-pyrimidin-2-yl-piperazin-1-yl) pentyloxy]-2H-[1,2,4]triazin-3-one (14)

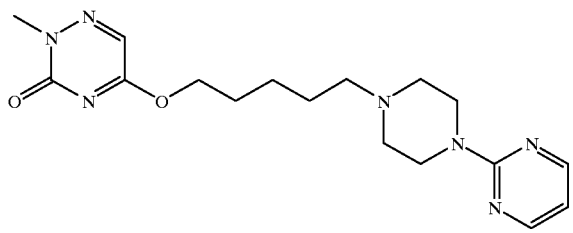

This compound is prepared according to the process described in Example 1, Stage f, using 4-(4-pyrimidin-2-yl-piperazin-1-yl)pentan-1-ol (prepared according to Process 2a from 5-choropentanol) and dioxane.

M.p.=98° C.; TLC, 60 F 254 Merck silica gel; $CH_2Cl_2$/MeOH/NH40H: 90/9/1, Rf=0.50.

EXAMPLE 15

5-[4-[4-(3-Methoxypyridin-2-yl)piperazin-1-yl] butoxy]-2-methyl-2H-[1,2,4]triazin-3-one fumarate (15)

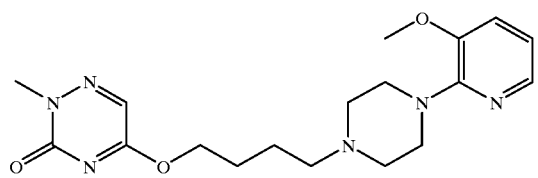

-continued

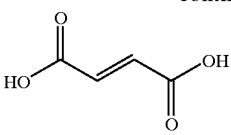

This compound is prepared according to the process described in Example 1, Stage f, using 4-(4-(3-methoxypyridin-2-yl)piperazin-1-yl)butan-1-ol (prepared according to Example 2a) and THF, and then salified with fumaric acid in ethanol.

M.p.=146° C.; TLC, 60 F 254 Merck silica gel; $CH_2Cl_2$/MeOH: 90/10, Rf=0.38.

EXAMPLE 16

5-[4-[4-(3-Chlorophenyl)piperazin-1-yl]Butoxy]-2-methyl-2H-[1,2,4]Triazin-3-one fumarate (16)

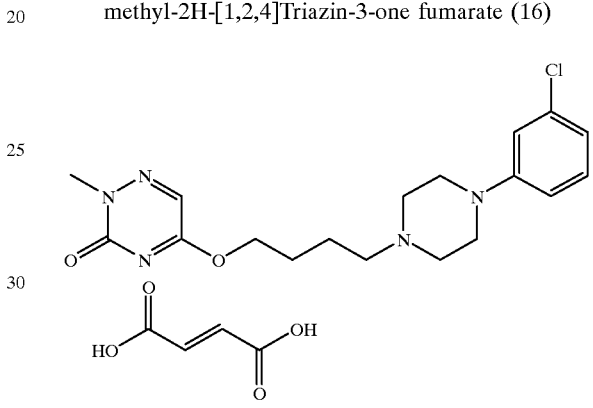

This compound is prepared according to the process described in Example 1 in Stage f using 4-(4-(3-chlorophenyl) piperazin-1-yl )butan-1-ol (prepared according to Example 2a) and dioxane, and then salified with fumaric acid in ethanol.

M.P.=153° C.; TLC, 60 F 254 Merck silica gel; $CH_2Cl_2$/MeOH: 90110, Rf=0.47.

EXAMPLE 17

5-[4-[4-(5-Chloro-2-methoxyphenyl)-piperazin-1-yl] butoxy]-2-methyl-2H- [1,2,4]triazin-3-one fumarate (17)

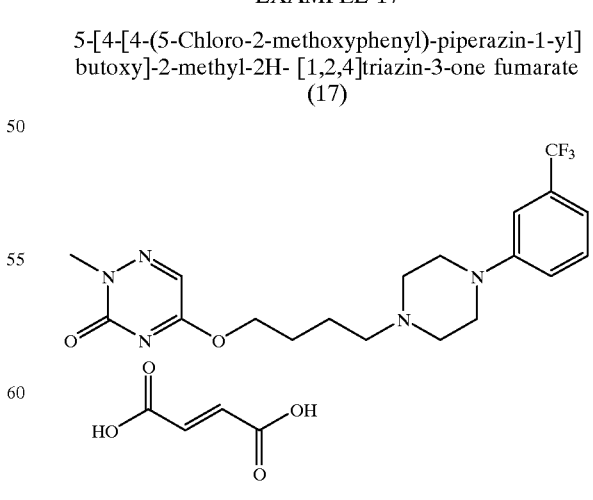

This compound is prepared according to the process described in Example 1 in Stage f using 4-(4-(3-

(trifluoromethyl)phenyl)piperazin-1-yl)butan-1-ol (prepared according to Example 2a) and dioxane, and then salified with fumaric acid in ethanol.

M.p.=184° C.; TLC, 60 F 254 Merck silica gel; CH$_2$Cl$_2$/MeOH: 90/10, Rf=0.65.

EXAMPLE 18

4-[4-[4-(2-Methyl-3-oxo-2,3-dihydro-[1,2,4]triazin-5-yloxy)Butyl]piperazin-1-yl]Benzonitrile (18)

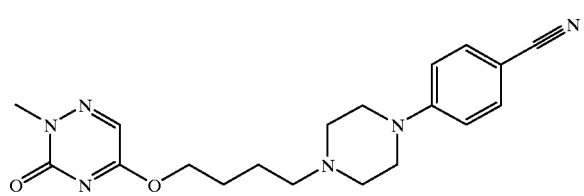

This compound is prepared according to the process described in Example 1 in Stage f using 4-(4-(4-hydroxybutyl)piperazin-1-yl)benzonitrile (prepared according to Example 2a) and dioxane.

M.p.=132° C.; TLC, 60 F 254 Merck silica gel; CH$_2$Cl$_2$/MeOH: 90/10, Rf=0.56.

EXAMPLE 19

5-[4-[4-(5-Chloro-2-methoxyphenyl)-piperazin-1-yl]butoxyl-2-methyl-2H-[1,2,4]triazin-3-one fumarate (19)

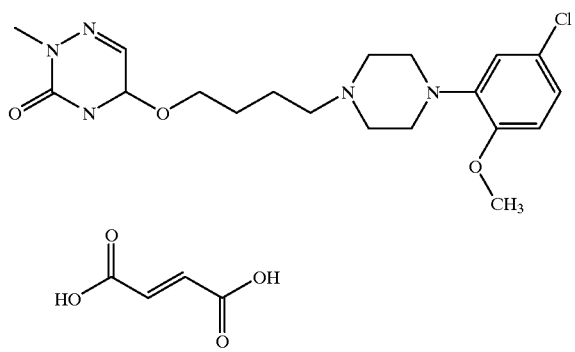

This compound is prepared according to the process described in Example 1 in Stage f using 4-(4-(5-chloro-2-methoxyphenyl)piperazin-1-yl)butan-1-ol (prepared according to Example 2a) and dioxane, and then salified with fumaric acid in methanol.

M.p.=149° C.; TLC, 60 F 254 Merck silica gel; CH$_2$Cl$_2$/MeOH: 90/10, Rf=0.54.

EXAMPLE 20

5-[4-((2,3-Dihydrobenzo[1,4]dioxin-2-ylmethyl)amino]butoxyl-2-methyl-2H-[1,2,4]triazin-3-one fumarate (20)

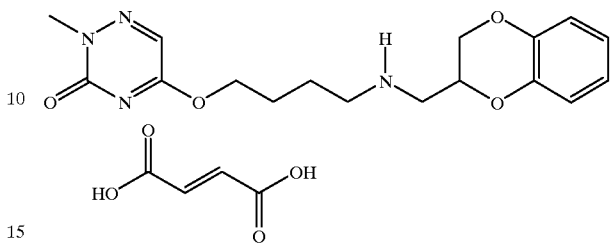

This compound is prepared according to Example 1 using C-(2,3-dihydrobenzo[1,4]dioxin-2-yl)methylamine in Stage d, and then salified with fumaric acid in ethanol.

M.p.=152° C.; TLC, 60 F 254 Merck silica gel; CH$_2$Cl$_2$/MeOH/NH$_4$OH: 90/9/1, Rf=0.58.

EXAMPLE 21

(R)-5-[4-[(2,3-Dihydrobenzo[1,4]dioxin-2-ylmethyl)amino]butoxy]-2-methyl-2H-[1,2,4]triazin-3-one fumarate (21)

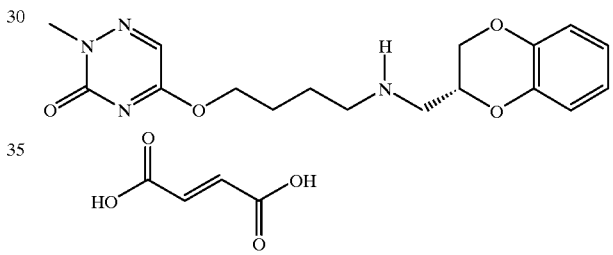

a) (R)-Trifluoromethanesulfonic acid -2,3-dihydro) benzo[1,4]dioxin-2-ylmethyl ester (21a)

(R)-(2,3-Dihydrobenzo[1,4]dioxin-2-yl)methanol (3.6 g, 21.7 mmol) is placed in 320 ml of dichloromethane at −5° C. Triflic anhydride (3.3 ml, 19.7 mmol) in 20 ml of CH$_2$Cl$_2$ is then run in dropwise. This mixture is stirred for 5 h at −5° C.

The reaction mixture is subsequently washed with 50 ml of 1N HCl and then with water. The organic phase is dried over MgSO$_4$ and then concentrated to dryness. The oil 21a obtained is used without further purification in the following stage.

b) (R)-4-[(2,3-Dihydrobenzo[1,4]dioxin-2-ylmethyl)amino]butan-1-ol (21b)

The compound 21a is placed in 30 ml of dichloromethane. 4-Aminobutanol (3.6 ml, 38.90 mmol), diluted in 10 ml of CH$_2$Cl$_2$, is then run dropwise into the reaction mixture. Stirring of the mixture is maintained for 14 h at room temperature.

The reaction mixture is concentrated to dryness and the residue is taken up in H$_2$O. After extracting with CH$_2$Cl$_2$, drying the organic phases over MgSO$_4$ and concentrating to dryness, an oil is isolated. It is purified by silica flash chromatography (eluent: CH$_2$Cl$_2$/MeOH/NH$_4$OH: 90/9/1) and 2.5 g of light-colored oil 21b are obtained.

TLC, 60 F 254 Merck silica gel; CH$_2$Cl$_2$/MeOH/NH4OH: 90/9/1, Rf=0.33.

c) (R)-5-[4-[(2,3-Dihydrobenzo[1,4]dioxin-2-ylmethyl) amino]butoxy)-2-methyl-2H-[1,2,4]triazin-3-one fumarate (21)

The final compound is obtained according to the process described in Example 1, Stage f, using the aminoalcohol 21b and dioxane, and then salified with fumaric acid in methanol.

M.p.=137° C.; TLC, 60 F 254 Merck silica gel; CH$_2$Cl$_2$/MeOH/NH40H: 90/9/1, RF=0.65.

EXAMPLE 22

(S)-5-[4-[(2,3-Dihydrobenzo[1,4]dioxin-2-ylmethyl) amino]butoxy]-2-methyl-2H-[1,2,4]triazin-3-one fumarate (22)

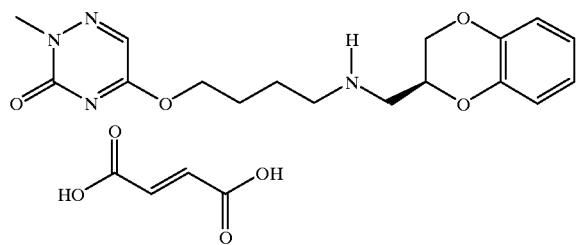

This compound is obtained according to the process described in Example 21 using (S)-(2,3-dihydrobenzo[1,4] dioxin-2-yl)methanol.

M.p.=135° C.; TLC, 60 F 254 Merck silica gel; CH$_2$Cl$_2$/MeOH/NH$_4$OH: 90/9/1, Rf=0.59.

EXAMPLE 23 trans-2-Methyl-5-(2-pyrimidin-2-yl-octahydropyrido [1,2-a]pyrazin-7-ylmethoxy)-2H-[1,2,4]triazin-3-one (23)

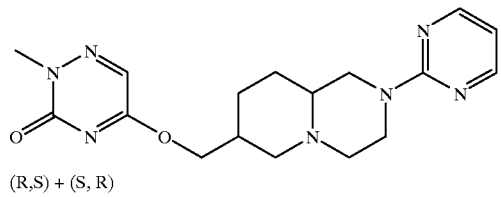
(R,S) + (S, R)

This compound is obtained according to the process described in Example 1 in Stage f using trans-2-pyrimidin-2-yl-octahydropyrido[1,2a]pyrazin-7-yl)-methanol and potassium tert-butoxide.

M.p.=140° C.; TLC, 60 F 254 Merck silica gel; CH$_2$Cl$_2$/MeOH: 90/10, Rf=0.35.

EXAMPLE 24 trans-2-Methyl-5-[2-(2-pyrimidin-2-yl-octahydropyrido 1,2-a]pyrazin-7-yl)ethoxy]-2H-1,2,4ltriazin-3-one (24)

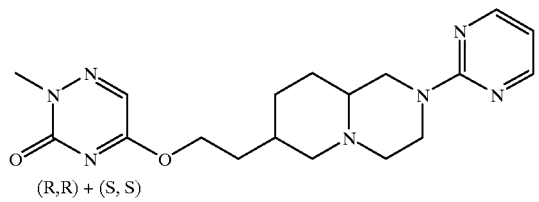
(R,R) + (S, S)

a) 2-Pyrimidin-2-yl-octahydropyrido[1,2-a]pyrazine-7-carbaldehyde (24a)

Oxalyl chloride (6.2 ml, 68.9 imol) is placed in 220 ml of dichioromethane at −50° C. DMSO (10 ml, 140.9 mmol), diluted in 25 ml of dichloromethane, is added. trans-(2-Pyrimidin-2-yl-octahydropyrido [1,2a)]-pyrazin-7-yl) methanol, diluted in 30 ml of CH$_2$Cl$_2$, is run dropwise onto this mixture maintained at −50° C.

After stirrring for 0.5 h at −50° C., triethylamine (40.8 ml, 293 mmol) is added and the temperature of the reaction mixture is brought back to room temperature.

The reaction mixture is washed with H$_2$O and then the organic phase is dried over MgSO$_4$ and then concentrated to dryness. The oil obtained 24a is purified by flash chromatography, CH$_2$Cl$_2$/MeOH: 90/10.

TLC, 60 F 254 Merck silica gel; CH$_2$Cl$_2$/MeOH/NH$_4$0H: 90/9/1, Rf=0.24.

b) (2-Pyrimidin-2-yl-octahydropyrido[1,2-a]pyrazin-7-yl) acetaldehyde (24b)

Methoxymethyltriphenylphosphonium chloride 41.4 g, 120.8 mmol) and dasopropylamine (11.6 ml, 88.5 mmol) are placed in 180 ml of THF at 0° C. under an inert atmosphere. n-Butyllithium (1.6M solution in THF, 55.2 ml, 88.3 mol) is run in dropwise and this mixture is stirred for 1 h at room temperature. The reaction mixture is brought back to 0° C. and 24a, diluted in 120 ml of THF, is run in dropwise. This mixture is stirred overnight at room temperature and then concentrated to dryness.

The residue is taken up in H$_2$O and extracted with ethyl acetate. The organic phases are washed with acidic H$_2$O (pH=1). This aqueous phase is washed with AcOEt, then brought back to pH 12 (concentrated NaOH solution) and extracted with dichloromethane. These organic phases are dried (MgSO$_4$) and then concentrated to dryness. The oil obtained is purified twice by silica flash chromatography (eluent: CH$_2$Cl$_2$/MeOH: 90/10 and AcOEt/acetone: 50/50). 6.3 g of yellow oil are recovered.

TLC, 60 F 254 Merck silica gel; CH$_2$Cl$_2$/MeOH/NH$_4$OH: 90/9/1, Rf=0.34.

c) 2-(2-Pyrimidin-2-yl-octahydropyrido[1,2-a]pyrazin-7-yl) ethanol (24c)

NaBH4 (1 g, 10.2 mmol) is placed in 30 ml of ethanol and then 24b (6.3 g, 24.2 mmol), diluted in 40 ml of ethanol, is run in dropwise. This mixture is stirred overnight at room temperature and then hydrolyzed with water.

After extraction with dichloromethane, the organic phases are dried (MgSO$_4$) and then concentrated to dryness. The residue obtained is purified by silica flash chromatography (eluent: CH$_2$Cl$_2$/MeOH: 90110). 4.5 g of yellow oil are recovered.

TLC, 60 F 254 Merck silica gel; CH$_2$Cl$_2$/MeOH: 90/10, Rf=0.12.

d) trans-2-Methyl-5-[2-(2-pyrimidin-2-yl-octahydropyrido[1,2-a]pyrazin-7-yl)ethoxy]-2H-[1,2,4]triazin-3-one (24)

This compound is obtained according to the process described in Example 1 in Stage f using the alcohol 24c and dioxane.

M.p.: 145° C.; TLC, 60 F 254 Merck silica gel; CH$_2$Cl$_2$/MeOH: 90/10, Rf=0.33.

EXAMPLE 25 trans-(−)-2-Methyl-5-[2-(2-pyrimidin-2-yl-octahydropyrido[1,2-a]pyrazin-7-yl)ethoxy]-2H-[1,2,4]triazin-3-one (25)

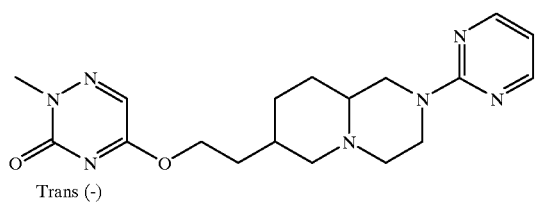

Trans (-)

The racemate prepared according to Example 24 is separated by preparative HPLC chromatography [silica grafted Chiracel OD-20 μm, eluent: hexane/isopropanol: 65/35 and 1/1000 of diethylamine]. An oil is isolated and again purified by flash chromatography (eluent: CH$_2$Cl$_2$/MeOH: 90/10). After crystallizing from an ether/isopropyl ether mixture, 0.31 g of white crystals is isolated.

M.p.=145° C.; TLC, 60 F 254 Merck silica gel; CH$_2$Cl$_2$/MeOH: 90/10, Rf=0.36.

EXAMPLE 26 trans-(+)-2-Methyl-5-12-(2-pyrimidin-2-yl-octahydropyrido[1,2-a)pyrazin-7-yl)ethoxy]-2H-[1,2,4]triazin-3-one (26)

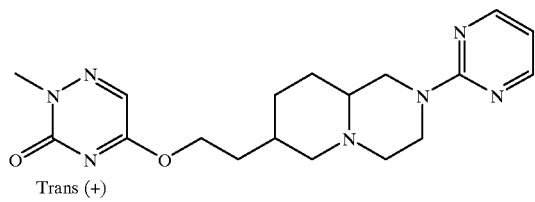

Trans (+)

This compound is isolated according to the process described in Example 25. 0.42 g of white solid is isolated.

M.p.=146° C.; TLC, 60 F 254 Merck silica gel; CH$_2$Cl$_2$/MeOH: 90/10, Rf=0.36.

EXAMPLE 27

2-Methyl-5-[4-(4-pyrimidin-2-yl-piperazin-1-yl)butylamino]-2H-[1,2,4]triazin-3-one (27)

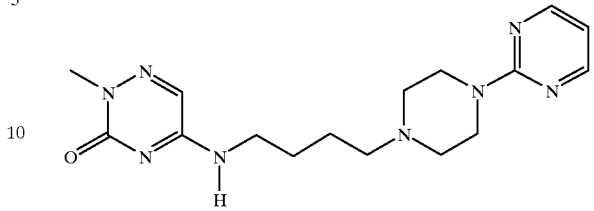

a) 4-(4-Pyrimidin-2-yl-piperazin-1-yl)butylamine (27a)

Pyrimidin-2-yl-piperazine dihydrochloride (17.5 g, 73.8 mmol) and 4-bromobutylphthalimide (25 g, 88 mmol) are placed in 200 ml of n-butanol and heated at reflux for 8 h. After concentrating the reaction mixture to dryness, the residue obtained is taken up in 100 ml of ethylenediamine and heated at reflux for 5 h.

The reaction mixture is concentrated under vacuum, the residue is taken up in basic H$_2$O (pH=11) and this aqueous phase is extracted with dichloromethane. The organic phases are dried over MgSO$_4$ and then concentrated to dryness. The residue obtained is purified by- silica flash chromatography (CH$_2$Cl$_2$/MeOH/NH$_4$OH: 90/9/1) and 10 g of oil, corresponding to the product 27a, are recovered.

TLC, 60 F 254 Merck silica gel; CH$_2$Cl$_2$/MeOH/NH$_4$OH: 80/18/2, Rf=0.24.

2-Methyl-5-[4-(4-pyrimidin-2-yl-piperazin-1-yl)butylamino]-2H-[1,2,4]triazin-3-one (27)

The amine 27a (2.2 g, 9.3 mmol) is placed in 30 ml of toluene in the presence of 1c (1.7 g, 11.2 mmol) and the mixture is heated at reflux for 4 h. The reaction mixture is concentrated to dryness under vacuum and the residue is taken up in H$_2$O/NaHCO$_3$ and extracted with dichloromethane. The aqueous phases are dried over MgSO$_4$ and then concentrated to dryness. The residue obtained is purified by silica flash chromatography (eluent: CH$_2$Cl$_2$/MeOH: 90/10) and 2.50 g of white crystals are obtained.

M.p.=188° C.; TLC, 60 F 254 Merck silica gel; CH$_2$Cl$_2$/MeOH: 90/10, Rf=0.26.

The compounds of the invention have been subjected to pharmacological tests which have demonstrated their advantage as therapeutically active substances.

Binding to the 5-HT$_{1A}$, D$_2$ dopaminergic and α1-adrenergic receptors:

Brains from male Sprague-Dawley 180–200 g rats [Ico: OFA SD (I.O.P.S. Caw); Iffa Credo, France], maintained at −70° C., were used in all the studies.

The affinity of the products for the various receptors was determined by displacement of radioactive ligands under the conditions summarized in Table 1.

The reaction is halted by rapid filtration, under vacuum, through Whatman GF/B filters and the tubes are rinsed with 2×5 ml of Tris-HCl 50 mM, pH 7.4, buffer at 25° C. The radioactivity collected on the filter is analyzed by liquid scintillation after addition of 4 ml of liquid scintillant (Emulsifier Safe, Packard). All the experiments are carried out in triplicate.

The inhibition constants (Ki) of the products are estimated from the displacement experimentations by using the EBDA (equilibrium binding data analysis) Radlig version 4 non-linear regression program (Biosoft, Cambridge, UK; McPherson, 1985).

The pKi (−log Ki) values are given in the form of the mean ± SEM of at least 3 experimentations (Table 2).

TABLE 1

Experimental conditions for binding to the receptors

| Binding site | [³H] ligand $K_D$ (nM) | Concentration (nM) | Tissue Type | Concentration | Incubation Time (min) | Temperature (° C.) | Nonspecific binding Product | Concentration (μM) | Buffer | References |
|---|---|---|---|---|---|---|---|---|---|---|
| 5-HT$_{1A}$ | 8-OH-DPAT (3.1) | 0.2 | cortex | 10 mg/ml | 30 | 23 | 5-HT | 10 | A | Assié et al., Eur. J. Pharmacol., 304, 15–21, 1996 |
| D$_2$ | YM-09151-2 (0.036) | 0.05 | striatum | 1 mg/ml | 60 | 23 | (+)-Butaclamol | 1 | B | Assié et al., Eur. J. Pharmacol., 237, 183–189, 1993 |
| α$_1$ | Prazosin (0.063) | 0.1 | cortex | 5 mg/ml | 30 | 23 | Phentolamine | 50 | C | Assié and Koek, Eur. J. Pharmacol., 304, 15–21, 1996 |

Buffers: (A) Tris HCl 50 mM pH 7.4, pargyline 10 μM, CaCl$_2$ 4 mM, 0.1% ascorbic acid; (B) Tris HCl 50 mM pH 7.4, NaCl 120 mM, KCl 5 mM; (C) Tris HCl 50 mM pH 7.4

TABLE 2

| | pKi | | |
|---|---|---|---|
| Compound No. | 5-HT$_{1A}$ | α$_1$ | D$_2$ |
| 1 | 9.17 | 6.25 | 5.80 |
| 2 | 9.57 | 6.11 | 5.76 |
| 3 | 9.56 | 6.01 | 5.95 |
| 4 | 9.86 | 6.74 | 5.65 |
| 6 | 9.68 | 6.25 | 5.77 |
| 7 | 9.04 | | |
| 15 | 9.58 | | |
| 16 | 10.12 | | |
| 17 | 9.89 | | |
| 19 | 9.51 | 8.21 | 7.82 |
| 20 | 9.97 | 7.65 | 7.18 |
| 21 | 9.48 | | |
| 22 | 10.47 | | |
| 24 | 9.28 | 6.35 | 5.54 |
| 26 | 9.61 | | |
| Buspirone | 7.65 | 6.19 | 7.49 |
| Flesinoxan | 8.91 | 6.50 | 7.05 |

Serotoninergic Syndrome:

The central activity of the compounds of the invention was evaluated by their ability to provoke the 5-HT syndrome, which is characterized by:
- an alternating bending and stretching of the forepaws (reciprocal fore-paw treading: FPT)
- the retraction of the lower lip (lower lip on: LLR)
- a position or the ventral surface of the animal is incobtact with the ground and the hind paws extended (flat body posture: FBP).

The experiments on the evaluation of the 5-HT syndrome are carried out with the male rat (Sprague-Dawley) according to the technique described by F. C. Colpaert et al. (Drug. Dev. Res, 26, 21–48, 1992) and M. S. Kleven et al. (J.P.E.T., 282, 747–759, 1997).

The active doses (ED$_{50}$) for some derivatives of the invention, in comparison with reference products such as Buspirone and Flesinoxan, are given in Table 3 by way of example.

TABLE 3

| | 5-HT syndrome | | |
|---|---|---|---|
| | ED$_{50}$ mg/kg po | | |
| Compound No. | FBP | LLR | FPT |
| 1 | 0.08 | 0.02 | 0.08 |
| 2 | 0.08 | 0.02 | 0.08 |
| 3 | 0.08 | 0.08 | 0.08 |
| 4 | 0.08 | <0.04 | 0.08 |
| 6 | 0.08 | 0.08 | 0.08 |
| 7 | 0.31 | 0.08 | 0.31 |
| 17 | 0.31 | 0.08 | 0.31 |
| 20 | 0.08 | <0.04 | 0.31 |
| 24 | 0.08 | <0.04 | 0.08 |
| 26 | <0.04 | <0.04 | 0.04 |
| Buspirone | 20 | 2.5 | >40 |
| Flesinoxan | 1.25 | 1.25 | 5 |

Antidepressant Activity: Forced Swimming Test:

The compounds of the invention are tested according to the procedure described by R. Porsolt et al. (Eur. J. Pharmacol., 47, 379–391, 1978).

The active doses (ED$_{50}$) are calculated for each compound according to the percentages of animals exhibiting a significant decrease, in comparison with the control animals ($p<0.05$), in the immobility time (Table 4).

TABLE 4

| Compound No. | ED$_{50}$ mg/kg po |
|---|---|
| 2 | 0.04 |
| 6 | 0.63 |
| 24 | 0.04 |
| 26 | 0.04 |
| Buspirone | >160 |
| Flesinoxan | 1.25 |

The results of the various tests show that the compounds of general formula I possess, in vitro, a high affinity for the serotoninergic receptors of 5-HT$_{1A}$ type and good selectivity with regard to α$_1$ and D$_2$ receptors. They show, in vivo, an agonist activity with regard to 5-HT$_{1A}$ receptors and are powerfully active with regard to behavioral models, such as the forced swimming test.

The compounds of the invention can therefore be of use in the treatment of anxiety, depression, pain, neurodegeneration, schizophrenia, Alzheimer's disease and sleep disorders, for the regulation of food intake, for the regulation of gastric secretion and for the treatment of vascular, cardiovascular and cerebrovascular disorders, such as hypertension or migraine.

The pharmaceutical preparations comprising compounds of general formula I as active principlg can be formulated for oral, rectal or parenteral administration, for example in the form of capsules, including hard gelatin capsules, tablets, granules, liquid solutions, syrups or suspensions to be taken orally, and can comprise the appropriate excipients.

It is also possible to combine therein other pharmaceutically and therapeutically acceptable active principles.

What is claimed is:

1. A 3-oxo-(2H)-1,2,4-triazine derivative selected from those of formula I

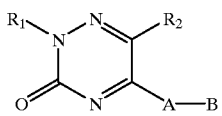

in which
r$_1$ represents:
    a linear or branched C$_1$–C$_4$ alkyl group or
    a phenyalkyl group, the phenyl nucleus optionally being substituted by one or more C$_1$–C$_4$ alkyl, C$_1$–C$_3$, alkoxy, halogen, and trifluoromethyl,
R$_2$ represents;
    hydrogen or
    a linear or branched C$_1$–C$_4$ alkyl radical or
    a phenyl or phenyalkyl group, the phenyl nucleus optionally being substitued by one or more C$_1$–C$_4$ alkyl, C$_1$–C$_3$ alkoxy, halogen, and trifluoromethyl,
A represents oxygen,
R$_3$ represents hydrogen or methyl,
B represents a group

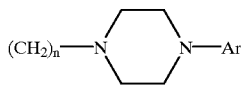

IIa in which Ar represents phenyl, pyridyl, or pyrimidyl, optionally substituted by one or more C$_1$–C$_3$ alkyl, C$_1$–C$_3$ alkoxy, hydroxyl, trifluoromethyl, and halogen, and n is 3 to5, in the form of a racemic mixture or an enantiomer or diastereoisomer thereof and pharmaceutically-acceptable inorganic or organic salts thereof.

2. A compound according to claim 1, chosen from the following compounds:

2-Methyl-5-[4-(4-pyrimidin-2-yl-piperazin-1-yl)butoxy]-2H-[1,2,4]triazin-3-one

2-Methyl-5-[4-[4-(4-methylpyrimidin-2-yl)piperazin-1-yl]butoxy]-2H-[1,2,4]triazin-3-one fumarate 5-[4-[4-(4,6-Dimethylpyrimidin-2-yl)piperazin-1-yl]butoxy]-2-methyl-2H-[1,2,4]triazin-3-one fumarate 5-[4-[4-(4-Methoxypyrimidin-2-yl)piperazin-1-yl]butoxy]-2-methyl-2H-[1,2,4]triazin-3-one fumarate 5-[4-(4-(5-Methoxypyrimidin-2-yl)piperazin-1-yl]butoxy]-2-methyl-2H-[1,2,4]triazin-3-one 5-14-[4-(4-Chloropyrimidin-2-yl)piperazin-1-yl]butoxy]-2-methyl-2H-[1,2,4]triazin-3-one 5-[4-[4-(5-Fluoropyrimidin-2-yl)piperazin-1-yl]butoxy]-2-methyl-2H-[1,2,4]triazin-3-one 2-Propyl-5-[4-(4-pyrimidin-2-yl-piperazin-1-yl)butoxy]-2H-[1,2,4]triazin-3-one fumarate 2,6-Dimethyl-5-[4-(4-pyrimidin-2-yl-piperazin-1-yl)butoxy]-2H-[1,2,4]triazin-3-one 2-Methyl-6-phenyl-5-[4-(4-pyrimidin-2-yl-piperazin-1-yl)butoxy]-2H-[1,2,4]triazin-3-one 2-Methyl-6-benzyl-5-[4-(4-pyrimidin-2-yl-piperazin-1-yl)butoxy]-2H-[1,2,4]triazin-3-one 2-Benzyl-5-[4-(4-pyrimidin-2-yl-piperazin-1-yl)butoxy]-2H-[1,2,4]triazin-3-one 2-Methyl-5-[3-(4-pyrimidin-2-yl-piperazin-1-yl)propoxy]-2H-[1,2,4]triazin-3-one fumarate 2-Methyl-5-[5-(4-pyrimidin-2-yl-piperazin-1-yl)pentyloxy]-2H-[1,2,4]triazin-3-one 5-[4-[4-(3-Methoxypyridin-2-yl)piperazin-1-yl]butoxy]-2-methyl-2H-[1,2,4]triazin-3-one fumarate 5-[4-[4-(3-Chlorophenyl)piperazin-1-yl]butoxy]-2-methyl-2H-[1,2,4]triazin-3-one fumarate 5-[4-[4-(5-Chloro-2-methoxyphenyl)piperazin-1-yl]butoxy]-2-methyl-2H-[1,2,4]triazin-3-one fumarate 4-[4-[4-(2-Methyl-3-oxo-2,3-dihydro-[1,2,4]triazin-5-yloxy)butyl]piperazin-1-yl]benzonitrile 5-[4-[4-(5-Chloro-2-methoxyphenyl)piperazin-1-yl]butoxy]-2-methyl-2H-[1,2,4]triazin-3-one fumarate 5-[4-[(2,3-Dihydrobenzo[1,4]dioxin-2-ylmethyl)amino]butoxy]-2-methyl-2H-[1,2,4]triazin-3-one fumarate (R)-5-[4-[(2,3-Dihydrobenzo[1,4]dioxin-2-ylmethyl)amino]butoxy]-2-methyl-2H-[1,2,4]triazin-3-one fumarate (S)-5-[4-[(2,3-Dihydrobenzo[1,4]dioxin-2-ylmethyl)amino]butoxy]-2-methyl-2H-[1,2,4]triazin-3-one fumarate trans-2-Methyl-5-(2-pyrimidin-2-yl-octahydropyrido[,2-a]pyrazin-7-ylmethoxy)-2H-[1,2,4]triazin-3-one trans-(−)-2-Methyl-5-[2-(2-pyrimidin-2-yl-octahydropyrido[1,2-a]pyrazin-7-yl)ethoxy]-2H-[1,2,4]triazin-3-one trans-(+)-2-Methyl-5-[2-(2-pyrimidin-2-yl-octahydropyrido[1,2-a]pyrazin-7-yl)ethoxy]-2H-[1,2,4]triazin-3-one; and 2-Methyl-5-[4-(4-pyrimidin-2-yl-piperazin-1-yl)butylamino]-2H-[1,2,4]triazin-3-one.

3. Process for the preparation of the a compound according to claim 1 wherein a compound of formula III

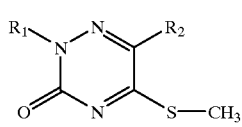

is treated with an alcohol B-OH IV R$_1$, R$_2$, R$_3$ and B being as defined in claim 1, in the presence of sodium hydride or of potassium tertbutoxide in dioxane, tetrahydrofuran or toluene.

4. Pharmaceutical composition, comprising, as active principle, a compound according to claim 1 in combination with a pharmaceutically acceptable excipient.

5. Pharmaceutical composition comprising a compound according to claim 2 in combination with a pharmaceutically-acceptable excipient.

6. Method of treating a living animal suffering from a disease requiring an agonist of 5-HT1A receptors wherein said disease is selected from anxiety, depression, schizophrenia, consisting of the step of administering to said animal an amount of a compound of claim 1 which is effective for amelioration of said disease.

7. Method of treating a living animal suffering from a disease requiring an agonist of 5-HT1A receptors wherein said disease is selected from anxiety, depression, schizophrenia, consisting of the step of administering to said animal an amount of a compound of claim 2 which is effective for amelioration of said disease.

* * * * *

UNITED STATES PATENT AND TRADEMARK OFFICE
CERTIFICATE OF CORRECTION

PATENT NO. : 6,303,603 B1
DATED : October 16, 2001
INVENTOR(S) : Jean-Francois Patoiseau et al.

Page 1 of 1

It is certified that error appears in the above-identified patent and that said Letters Patent is hereby corrected as shown below:

Title page,
ABSTRACT,
Line 2, " $_1$ - C$_4$" should read -- C$_1$ - C$_4$ --.
Line 6, "C$_1$ - C$_4$ phenyl" should read -- C$_1$ - C$_4$ phenyl --.

Column 24,
Line 3, "5-[4-(4-(" should read -- 5-[4-[4-( --.
Line 44, please add the number -- 1 -- (one) after "octahydropyrido[ ".
Line 54, please remove the word "the" that appears after the phrase "Process for the preparation of".

Signed and Sealed this

Seventh Day of May, 2002

*Attest:*

JAMES E. ROGAN
*Attesting Officer*    *Director of the United States Patent and Trademark Office*